United States Patent [19]

Seiler

[11] 4,387,007

[45] Jun. 7, 1983

[54] PROCESS FOR THE MANUFACTURE OF AN ALDEHYDE

[75] Inventor: Peter Seiler, Aesch, Switzerland

[73] Assignee: Hoffmann-La Roche Inc., Nutley, N.J.

[21] Appl. No.: 207,824

[22] Filed: Nov. 17, 1980

[51] Int. Cl.$^3$ .............................................. C25B 3/02
[52] U.S. Cl. .................................... 204/59 R; 204/78
[58] Field of Search ............................... 204/59 R, 78

[56] References Cited

U.S. PATENT DOCUMENTS

| | | | |
|---|---|---|---|
| 3,836,441 | 9/1974 | Millington | 204/78 |
| 4,148,696 | 4/1979 | Halter . | |
| 4,212,711 | 7/1980 | Halter et al. | 204/78 |
| 4,235,683 | 11/1980 | Degner et al. | 204/78 |
| 4,318,783 | 3/1982 | Buhmann et al. | 204/59 R |

FOREIGN PATENT DOCUMENTS 2351932 12/1977 France .

OTHER PUBLICATIONS

Helv. Chem. Acta 9, 1097–1101, (1926).

Primary Examiner—Howard S. Williams
Attorney, Agent, or Firm—Jon S. Saxe; George M. Gould; Peter R. Shearer

[57] ABSTRACT p-Tert. butylbenzaldehyde is manufactured by the electrochemical oxidation of p-tert. butyltoluene, an intermediate for the production of e.g. α-methyl-β-(p-tert. butylphenyl)-propionaldehyde.

28 Claims, No Drawings

PROCESS FOR THE MANUFACTURE OF AN ALDEHYDE

BACKGROUND OF INVENTION

The compound, p-tert. butylbenzaldehyde, has hitherto been manufactured by oxidizing p-tert.butyltoluene with chemical oxidation agents, especially with manganese dioxide. This chemical oxidation process of the prior art has serious disadvantages, especially with respect to the manganese salts which separate out in large amounts. Furthermore, the manganese dioxide which is used is not supplied in constant quality but rather in very variable quality, which naturally does not enable the process to be carried out uniformly.

The anodic oxidation in accordance with the present invention avoids the disadvantages associated with the use of manganese dioxide as the chemical oxidation agent and permits p-tert.butylbenzaldehyde to be manufactured in a simple manner and in high yields. Moreover, hydrogen results at the cathode as a very useful byproduct.

DESCRIPTION OF THE INVENTION

The present invention relates to a process for producing p.tert-butylbenzaldehyde from p-tert-butyltoluene by electrochemical oxidation.

The process of the present invention may be carried out in any art recognized electrolytic cell which includes both undivided and sub-divided ones, having the basic essential elements of electrodes and electrolyte in a container. In the case of a subdivided electrolytic cell, the sub-division of the cell may be effected by any art recognized material suitable for carrying out electrolysis, such as membranes or diaphragms made of art recognized membrane or diaphragm materials.

The electrodes, i.e. the anode and the cathode, may have any art recognized form. For example the electrodes may be in the form of plates, lattices or expanded metal. The anode may be of any material suitable for carrying out the electrochemical oxidation process provided by this invention. The preferred material for the anode is a metal oxide such as lead dioxide, manganese dioxide, or a metal oxide-titanium composite; or a noble metal such as platinum or platinised titanium; or graphite.

The most preferred material for the anode is the metal oxide-titanium composite, providing a metal oxide-titanium composite anode. Said composite anodes consist of a carrier of titanium which is provided with a metal oxide coating. An intermediate layer of a carbide or boride of an element of the IVth and Vth sub-groups of the Periodic Table of the Elements is applied to the titanium surface before the application of the metal oxide coating. A particular composite anode, namely a lead dioxide-titanium composite anode, as well as its manufacture, is described in German Patent Specification No. 2722840. The preferred metal oxide-titanium composite anode is the lead dioxide-titanium composite anode.

Manganese dioxide, when used as the anode material, may be applied either to graphite, lead or lead dioxide.

The cathode may be of any material suitable for reduction in combination with the anode oxidation in the process of the present invention. Suitable cathode materials include for example steel, nickel and copper.

The electrolyte may be any art recognized solvent permitting flow of a current and dissolving the starting material, ptert.butyltoluene. Among the electrolytes that may be used are any aqueous acids. Art recognized non-oxidative mineral acids are preferred, with the most preferred being sulphuric acid. The preferred concentration of sulphuric acid in water is from about 5 to about 50% by volume, with the most preferred being 7.5 to 15%.

The electrolysis may be carried out in a reaction mixture of aqueous mineral acid and ptert.butyltoluene with no additional solvent being required. The preferred reaction mixture, however, contains an aqueous mineral acid, p-tert.butyltoluene and an inert organic solvent. Any suitable inert organic solvent may be used, suitable ones being for example a hydrocarbon such as dichlorethane or methylene chloride, or a tertiary lower alkanol such as tert-butanol ar acetone. The most preferred inert organic solvent is acetone. The concentration of inert organic solvent in the reaction mixture of aqueous mineral acid and p-tert.butyltoluene is from about 10 to about 60% by volume.

When the reaction mixture contains an organic solvent which is not miscible with water or when the electrolysis is carried out in the absence of an additional solvent (i.e. using the starting material as the solvent), a phase transfer catalyst (e.g. diodecyl hydrogen sulphate sodium salt or a tetraalkylammonium salt such as tetrabutylammonium hydrogen sulphate) is preferably used.

When metal oxide anodes, especially metal oxide composite anodes, are used, it has been found to be preferred to use dichlorethane as the solvent, while when graphite anodes are used it has been found to be especially advantageous to use acetone as the solvent.

Especially when graphite anodes are used there are formed, in addition to the desired p-tert.butylbenzaldehyde, small amounts of p-tert. butylbenzyl alcohol. This alcohol can be separated by distillation and returned to the process, i.e. admixed with the p-tert.butyltoluene starting material.

The concentration of the starting material in the electrolyte mixture used can, in general, vary between about 1% and 80%, especially between about 10% and 50%, preferably between about 10% and 20% (vol.-/vol.).

The temperature at which the present process is carried out is not critical. It is, however, defined at the upper limit by the boiling point of the solvent. In general, the present process is carried out at between room temperature and about 80° C., especially between room temperature and about 60° C. The temperature can be maintained at the desired limits by art recognized cooling procedures.

Metal salts, for example manganous salts such as manganous sulphate or cerous salts such as cerous sulphate, can be added to the electrolytes in a manner known per se; namely in only small amounts, for example in an amount of about 1% based on the amount of the batch.

The voltages and current intensities used are governed by the solvent used, by the size of the cell and by the current density used. In general, the electrolysis is carried out using a voltage between about 3 and about 20 V. The current density can vary within wide limits, the current densities generally amounting to between about 0.01 mA and about 100 mA per $cm^2$, especially between about 0.4 mA and about 50 mA per $cm^2$.

Typically the process of the present invention provides for the production of p-tert.butylbenzaldehyde by an electrochemically oxidizing reaction. p-tert.butyltoluene is added to a mixture of an inert organic solvent and a non-oxidative mineral acid in a glass container. An anode of lead dioxide-titanium composite and a cathode of a nickel wire are placed within the mixture and connected at a suitable distance. A voltage is applied between the electrodes while temperature is held suitably by external cooling. Vigorous intermixing of the mixture should be carried out during the electrolysis. After electrolysis is discontinued, the resulting reaction mixture is extracted with chloroform to obtain p-tert.butylbenzaldehyde.

The following Examples further illustrate the invention but are not meant to limit the invention in scope or spirit.

EXAMPLE 1

2.5 ml of p-tert.butyltoluene, 10 ml of dichloroethane and 110 ml of 10N sulphuric acid are emulsified while stirring magnetically in a glass vessel provided with a cover. Expanded titanium metal (5×5 cm) coated with lead dioxide [lead dioxide-titanium composite electrode described in "Zeitschrift fur Naturforschung" 31 b, 39-50 (1976)] is used as the anode and the cathode is a nickel wire at a distance of 3 cm from the anode. A voltage of 3.4 volt is applied between the electrodes, whereupon a current of 50 mA is set. The temperature is held at 25° C. by external cooling. After the throughput of 1.55 aH, corresponding to 100% of the theoretically required current, the electrolysis is discontinued. The solution is extracted three times with 60 ml of chloroform each time and the combined extracts are analysed quantitatively by gas chromatography. With a conversion of 83% there is obtained a yield of p-tert.butylbenzaldehyde which amounts to 77% of theory.

EXAMPLE 2

A solution of 2.5 ml of p-tert.butyltoluene in 40 ml of 3N aqueous sulphuric acid and 80 ml of acetone is electrolysed at room temperature, with 0.75 A current intensity and 7.8–8.5 V voltage and while stirring in an undivided electrolysis cell which is provided with a graphit foil of 25 cm² surface as the anode and a nickel wire as the cathode. After completion of the electrolysis (after 2 hours), a sample is removed and extracted with chloroform. The products are determined by gas chromatography. With a conversion of 79% the yield of p-tert.butylbenzaldehyde (based on reacted p-tert.butyltoluene) amounts to 60 mol %, the yield p-tert.butylbenzyl alcohol amounts to 10 mol %.

I claim:

1. A process for producing p-tert-butyl-benzaldehyde, comprising electrochemically oxidizing in an electrolytic cell containing electrolyte and anode and cathode electrodes, a composition consisting of p-tert-.butyltoluene.

2. A process according to claim 1, wherein a metal oxide anode is used.

3. A process according to claim 2, wherein a lead dioxide anode is used.

4. A process according to claim 1, wherein a metal oxide-titanium composite anode is used.

5. A process according to claim 4, wherein the anode is a lead dioxide-titanium composite anode.

6. A process according to claim 1, wherein a graphite anode is used.

7. A process for producing p-tert-butyl-benzaldehyde, comprising electrochemically oxidizing in an electrolytic cell containing an electrolyte and anode and cathode electrodes, a composition consisting of p-tert-.butyltoluene and an inert organic solvent.

8. A process according to claim 7, where a metal oxide anode is used.

9. A process according to claim 8 wherein, a lead dioxide anode is used.

10. A process according to claim 7, wherein a metal oxide-titanium composite anode is used.

11. A process according to claim 10, wherein the anode is a lead dioxide-titanium composite anode.

12. A process according to claim 7, wherein a graphite anode is used.

13. A process according to claim 7, wherein the anode is a lead dioxide anode and the inert organic solvent is dichloroethane.

14. A process according to claim 7, wherein the anode is a graphite anode and the inert organic solvent is acetone.

15. A process for producing p-tert-butyl-benzaldehyde, comprising electrochemically oxidizing in an electrolytic cell containing an electrolyte and anode and cathode electrodes, a compositions consisting of p-tert-.butyltoluene and a phase transfer catalyst.

16. A process according to claim 15, wherein a metal oxide anode is used.

17. A process according to claim 16, wherein a lead dioxide anode is used.

18. A process according to claim 15, wherein a metal oxide-titanium composite anode is used.

19. A process according to claim 18, wherein the anode is a lead dioxide-titanium composite anode.

20. A process according to claim 15, wherein a graphite anode is used.

21. A process according to claim 15, wherein the phase transfer catalyst is diodecyl hydrogen sulphate sodium salt or a tetraalkylammonium salt.

22. A process according to claim 21, wherein the tetraalkylammonium salt is tetrabutylammonium hydrogen sulphate.

23. A process for producing p-tert-butyl-benzyldehyde, comprising electrochemically oxidizing in an electrolytic cell containing an electrolyte and anode and cathode electrodes, a composition consisting of p-ter.-butyltoluene, a phase transfer catalyst and a water immiscible organic solvent.

24. A process according to claim 23, wherein a metal oxide anode is used.

25. A process according to claim 24, wherein a lead dioxide anode is used.

26. A process according to claim 23, wherein a metal oxide-titanium composite anode is used.

27. A process according to claim 26, wherein the anode is a lead dioxide-titanium composite annode.

28. A process according to claim 23, wherein the anode is a lead dioxide anode and the water immiscible solvent is dichloroethane is used as an inert organic solvent.

* * * * *